United States Patent [19]

Shoesmith, deceased

[11] Patent Number: Plant 6,112

[45] Date of Patent: Feb. 23, 1988

[54] CHRYSANTHEMUM PLANT NAMED MYSTIC

[75] Inventor: Leonard H. Shoesmith, deceased, late of Westfield, England, by May Victoria Shoesmith, executrix

[73] Assignee: Ball PanAm Plant Company, Parrish, Fla.

[21] Appl. No.: 712,698

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Mystic having a dwarf habit, flat capitulum form and spoon single capitulum type, dark lavender-purple color, eight week response, and an ability to be grown year around in 9 cm. pots with little growth regulation.

2 Drawing Figures

The present invention comprises a new and distinct cultivar of *Chrysanthemum morifolium,* Ramat., hereinafter referred to by the cultivar name Mystic.

Mystic is a product of a planned breeding program which had the objective of creating new Chrysanthemum cultivars with eight (8) week response, lavender spoon type daisy flowers, and dwarf habit suitable for year around growing in 9 cm. pots. Such traits in combination were not present in previously available commercial cultivars.

Mystic was originated from a hybridization made by Leonard H. Shoesmith in a controlled breeding program in Westfield, Woking, England in 1978. The male and female parents are unknown at this time. Mystic was discovered and selected as one flowering plant within the progeny of the parentage by applicant in November, 1979 in a controlled environment in West Chicago, Ill., and given the code name F9-1856-PS.

The first act of asexual reproduction of Mystic was accomplished when vegetative cuttings were taken from the initial selection in February, 1980 in a controlled environment in West Chicago, Ill. by a technician working under formulations established and supervised by Leonard H. Shoesmith. Horticultural examination of selected units initiated in March, 1980 has demonstrated that the combination of characteristics as herein disclosed for Mystic are firmly fixed and are retained through successive generations of asexual reproduction.

Mystic has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Mystic, which in combination distinguish this Chrysanthemum as a new and distinct cultivar:

1. Flat capitulum form.
2. Spoon single capitulum type.
3. Dark lavender-purple color.
4. Dwarf habit, extending 10–15 cm. above edge of pot.
5. Eight (8) week response.

6. Ability to be grown year around in 9 cm. pots in most areas, and requiring few B-9 treatments.

Of the many commercial cultivars known to the present inventor, the most similar in comparison to Mystic is the cultivar Fantasy, disclosed in U.S. Plant Pat. No. 4,469. In comparison to Fantasy, Mystic has a darker lavender-purple color, is much shorter and more suitable for 9 cm. pots, is more fade resistant, and is less temperature sensitive. The flower form and type of Mystic are similar to those same characteristics of Fantasy.

The accompanying drawings show typical inflorescence and foliage characteristics of Mystic, with colors being as nearly true as possible with illustrations of this type.

Sheet 1 is a color photograph showing several flowers.

Sheet 2 is a black and white photograph on which two flowers have been colored to accurately depict true ray and floret colors.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., cv Mystic.

*Commercial.*—Spoon daisy spray, four (4) inch pot.

INFLORESCENCE

A. Capitulum:

*Form.*—Flat.

*Type.*—Spoon Daisy.

*Diameter across face.*—3–5 cm.

B. Corolla of ray florets:

*Color (general tonality from a distance of three meters).*—Dark lavender-purple.

*Color (under surface).*—70 C.

*Color (top surface).*—Spoon 70 A, tube 70 C.

C. Corolla of disc florets:

*Color (mature).*—Yellow.

*Color (immature).*—Lime green.

D. Reproductive organs:

*Androecium.*—Present in disc florets only; numerous.

*Gynoecium.*—Present in both ray and disc florets; numerous.

PLANT

A. General appearance:

*Height.*—10–15 cm. above edge of pot when properly grown in 9 cm. pot.

B. Foliage:

*Color (under surface).*—147 B.

*Color (top surface).*—147 A.

*Shape.*—Ovate and deeply lobed.

It is claimed:

1. A new and distinct cultivar of chrysanthemum named Mystic, as described and illustrated, and particularly characterized by its dwarf habit; flat capitulum form and spoon single capitulum type; dark lavender-purple color; eight week response, and by its ability to be grown year around in 9 cm. pots with little growth regulation.

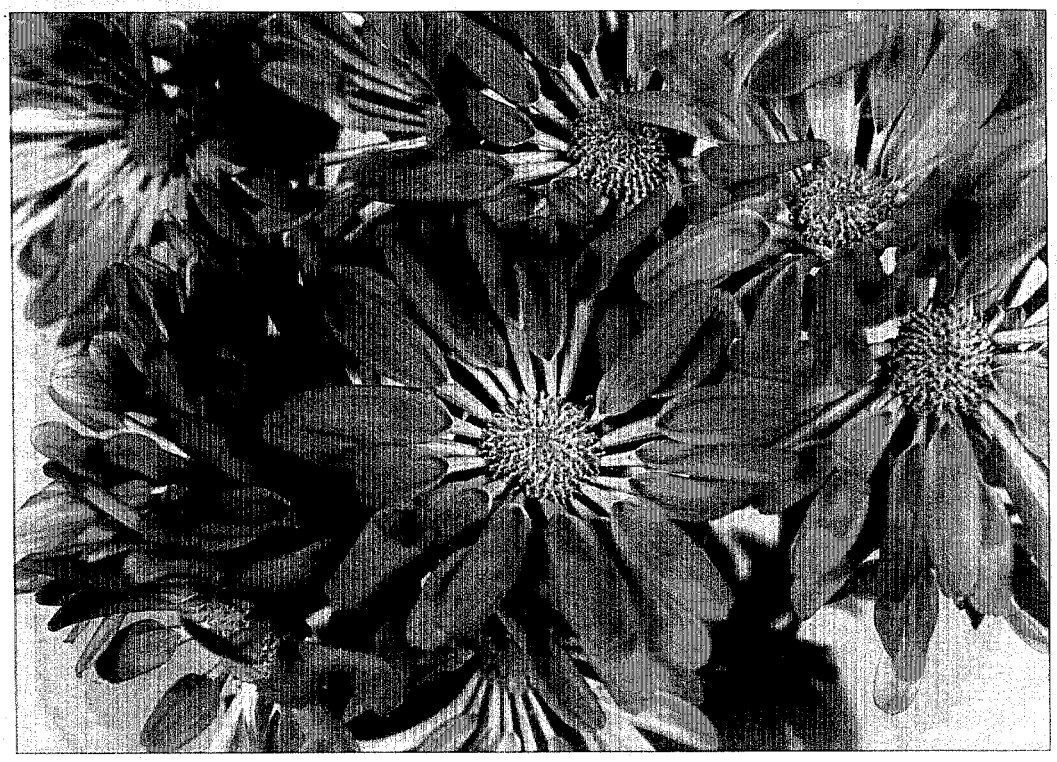

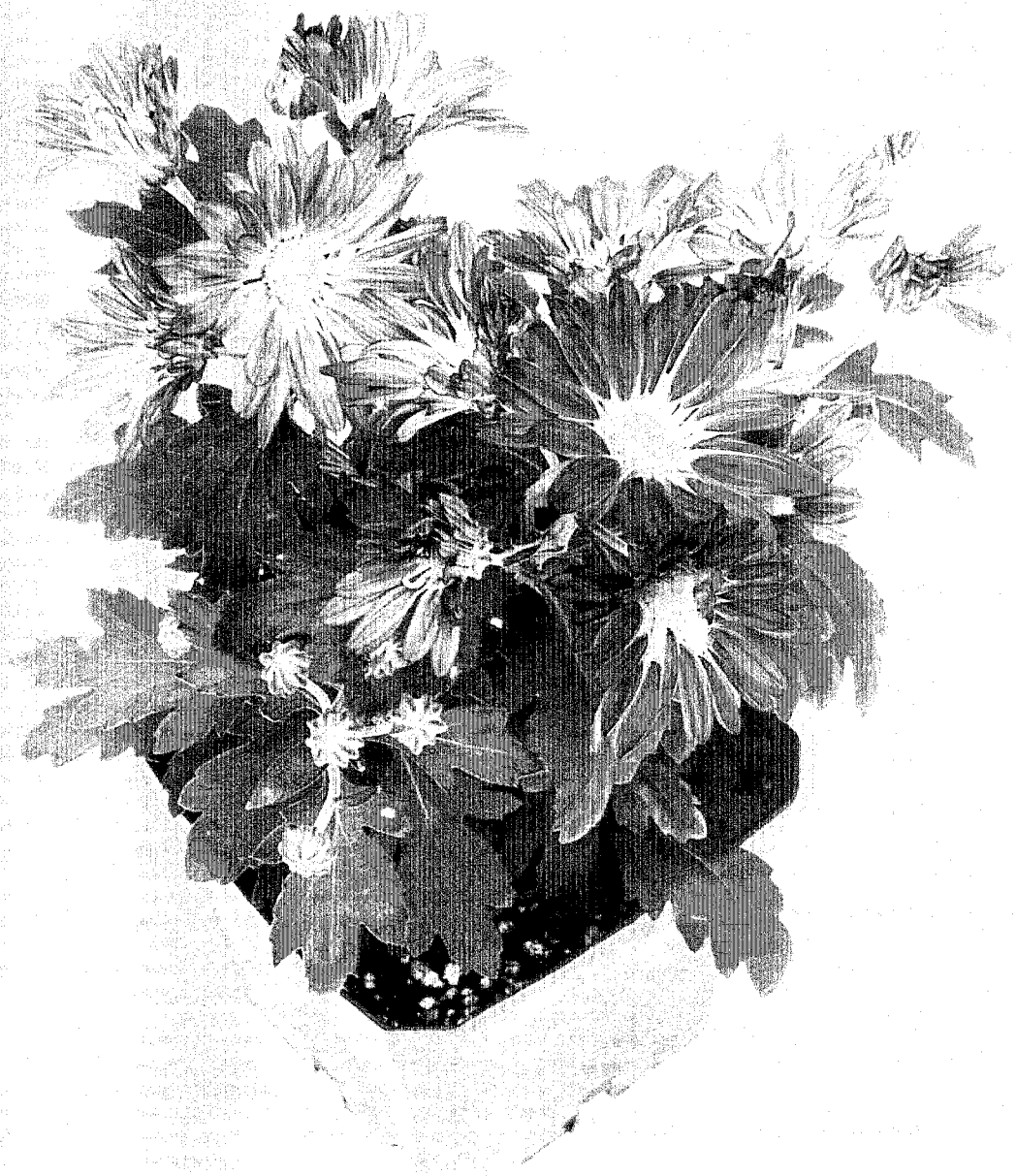

* * * * *